(12) United States Patent
Novo et al.

(10) Patent No.: US 11,319,288 B2
(45) Date of Patent: May 3, 2022

(54) METHOD FOR THE PREPARATION OF PIMAVANSERIN BASE

(71) Applicant: OLON S.P.A., Rodano (IT)

(72) Inventors: Barbara Novo, Rodano (IT); Jacopo Bonanomi, Rodano (IT); Mattia Bertolotti, Rodano (IT)

(73) Assignee: OLON S.P.A., Rodano (IT)

( * ) Notice: Subject to any disclaimer, the term of this patent is extended or adjusted under 35 U.S.C. 154(b) by 12 days.

(21) Appl. No.: 17/049,682

(22) PCT Filed: Apr. 24, 2019

(86) PCT No.: PCT/IB2019/053366
§ 371 (c)(1),
(2) Date: Oct. 22, 2020

(87) PCT Pub. No.: WO2019/207494
PCT Pub. Date: Oct. 31, 2019

(65) Prior Publication Data
US 2021/0130296 A1 May 6, 2021

(30) Foreign Application Priority Data

Apr. 26, 2018 (IT) .................. 102018000004891

(51) Int. Cl.
*C07D 211/58* (2006.01)
(52) U.S. Cl.
CPC .................. *C07D 211/58* (2013.01)
(58) Field of Classification Search
CPC .................................................. C07D 211/58
See application file for complete search history.

(56) References Cited

U.S. PATENT DOCUMENTS

2019/0047955 A1\* 2/2019 Carlos .................. C07D 211/58

FOREIGN PATENT DOCUMENTS

WO 2017015272 A1 1/2017

OTHER PUBLICATIONS

Search Report and Written Opinion of PCT/IB2019/053366 dated Jul. 24, 2019.
Spyropoulos C. et al., "One-pot synthesis of ureas from Boc-protected amines", Journal of organic chemistry, vol. 79, No. 10, Apr. 21, 2014, pp. 4477-4483.

\* cited by examiner

*Primary Examiner* — Timothy R Rozof
(74) *Attorney, Agent, or Firm* — Silvia Salvadori, P.C.; Silvia Salvadori

(57) ABSTRACT

Disclosed is a process for the synthesis of pimavanserin base with a high yield and purity, which comprises: a) converting tert-butyl-N-[(4-propan-2-yloxyphenyl)methyl]carbamate (Formula (I)) to 1-(isocyanatomethyl)-4-propan-2-yloxy-benzene of formula (II) b) adding N-[(4-fluorophenyl)methyl]-1-methylpiperidin-4-amine (Formula (IV)) to the solution obtained in a) to give pimavanserin base, and c) purifying the pimavanserin base obtained in step b).

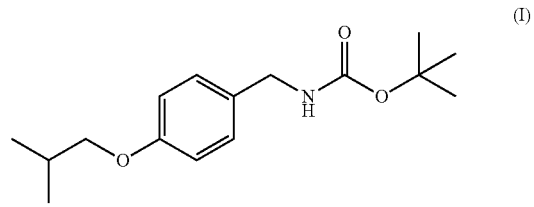

(I)

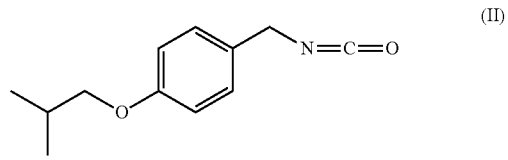

(II)

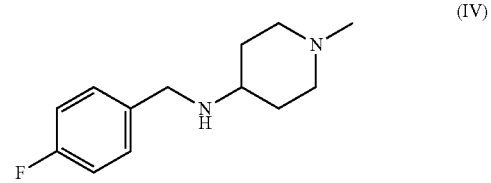

(IV)

8 Claims, No Drawings

METHOD FOR THE PREPARATION OF PIMAVANSERIN BASE

This application is a U.S. national stage of PCT/IB2019/053366 filed on 24 Apr. 2019, which claims priority to and the benefit of Italian Application No. 102018000004891 filed on 26 Apr. 2018, the contents of which are incorporated herein by reference in their entireties.

FIELD OF INVENTION

The present invention relates to a process for the synthesis of pimavanserin base with high purity.

BACKGROUND TO THE INVENTION

N-azacycloalkyl-N-arylalkyl carbamide compounds are serotonin 5-HT receptor inverse agonists.

In particular, pimavanserin hemitartrate is highly selective for the $5HT_{2A}$ receptor, with an affinity 40 times greater than for the $5\text{-}HT_{2B}$ receptor, whereas it has no affinity for the $5\text{-}HT_2c$ receptors or the dopamine receptors. WO 2008/144665 describes the use of N-(4-fluorobenzyl)-N-(1-methylpiperidin-4-yl)-N'-(4-(2-methylpropyloxy)phenyl-methyl) carbamide hemitartrate for the treatment of psychosis and schizophrenia in patients suffering from Parkinson's disease. Pimavanserin hemitartrate exhibits greater efficacy and fewer side effects than other antipsychotics. Moreover, the administration of pimavanserin in combination with other antipsychotics, such as haloperidol and risperidone, improves the tolerability of the treatment by reducing the incidence of side effects. Pimavanserin hemitartrate is obtained by reacting pimavanserin base in ethanol with the addition of (L)-(+) tartaric acid (U.S. Pat. No. 7,790,899).

The synthesis of pimavanserin base is described in U.S. Pat. No. 7,790,899 (Scheme 1) and U.S. Pat. No. 7,601,740 (Scheme 2).

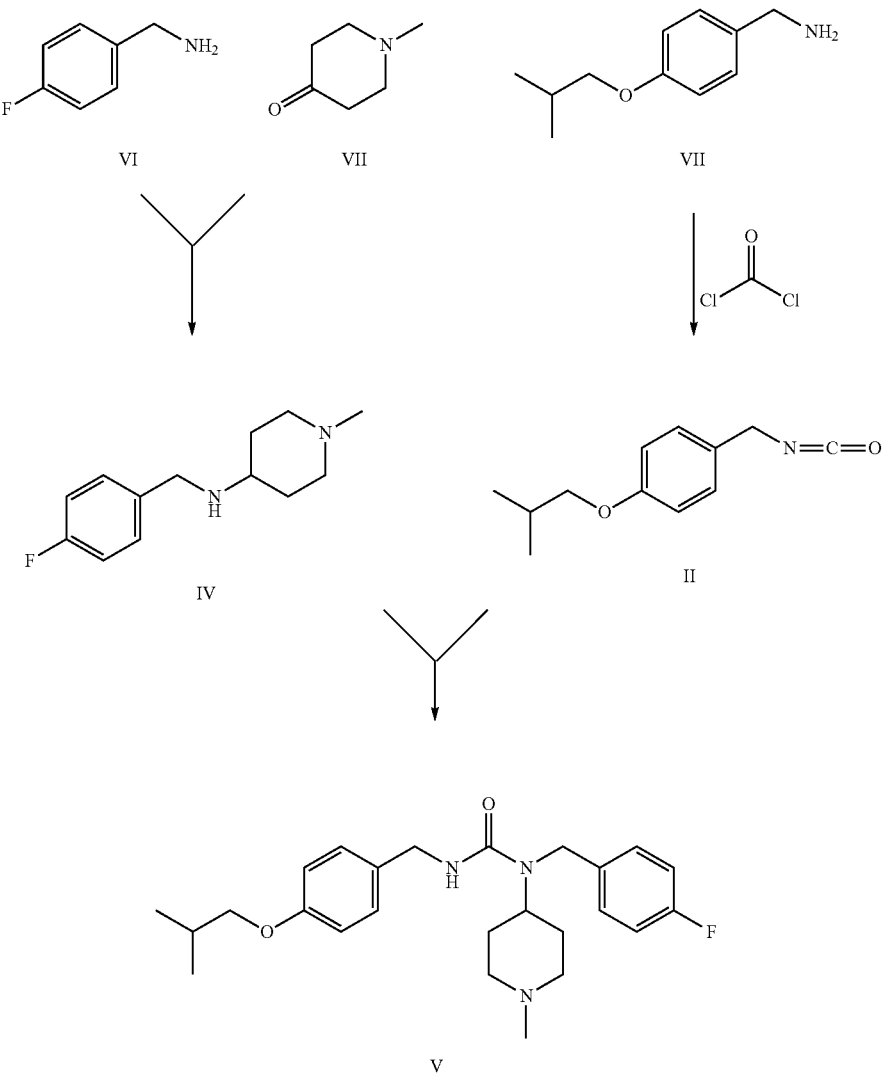

Scheme 1

U.S. Pat. No. 7,790,899 describes the synthesis of pimavanserin (V) via the formation of 1-(isocyanatomethyl)-4-propan-2-yloxybenzene (II), obtained by reacting [4-(2-methylpropoxy)phenyl]methanamine (VIII) with phosgene. The main drawback of said procedure relates to the use of a highly unstable, hazardous, unmanageable reagent like phosgene. Moreover, said synthesis method involves the isolation of 1-(isocyanatomethyl)-4-propan-2-yloxybenzene (II), which is also hazardous and unmanageable.

All the procedures employed in the above-mentioned documents involve the use of hazardous reagents such as phosgene derivatives or diphenylphosphoryl azide.

Patent application WO2017015272 describes an alternative method for synthesising pimavanserin by reacting an N[(4-propan-2-yloxyphenyl)methyl]-amine carbamate with N-[(4-fluorophenyl)methyl]-1-methylpiperidin-4-amine in the presence of catalytic quantities of DMPA (dimethylamino pyridine).

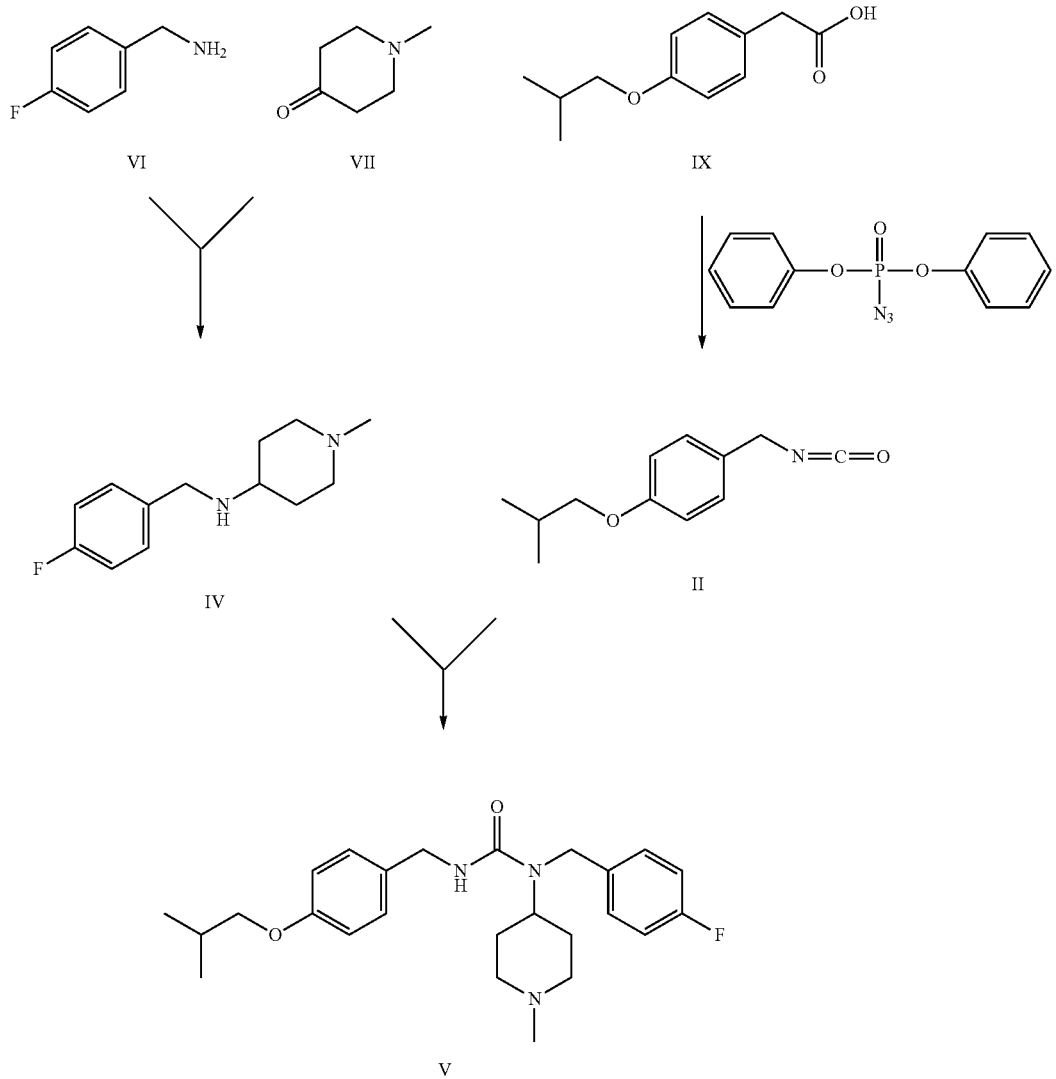

Scheme 2

U.S. Pat. No. 7,601,740 describes the formation of 1-(isocyanatomethyl)-4-propan-2-yloxybenzene (II) by reacting 2-[4-(2-methylpropoxy)phenyl]acetic acid (IX) with diphenylphosphoryl azide. The main drawback of said procedure relates to the use of a highly toxic, hazardous, explosive reagent like diphenylphosphoryl azide.

Other pimavanserin synthesis processes are described in JP2013087107, Bioorganic & Medicinal Chemistry (21, 2960-2967, 2013), Synthesis (1955-1958, 2005) and Turkish Journal of Chemistry (31, 35-43, 2007).

Scheme II: SM1 plus SM2 Carbamate Pimavanserin Synthesis

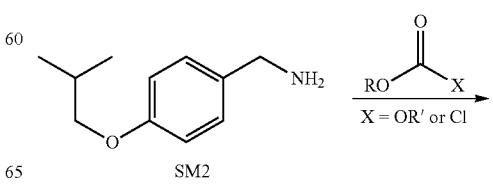

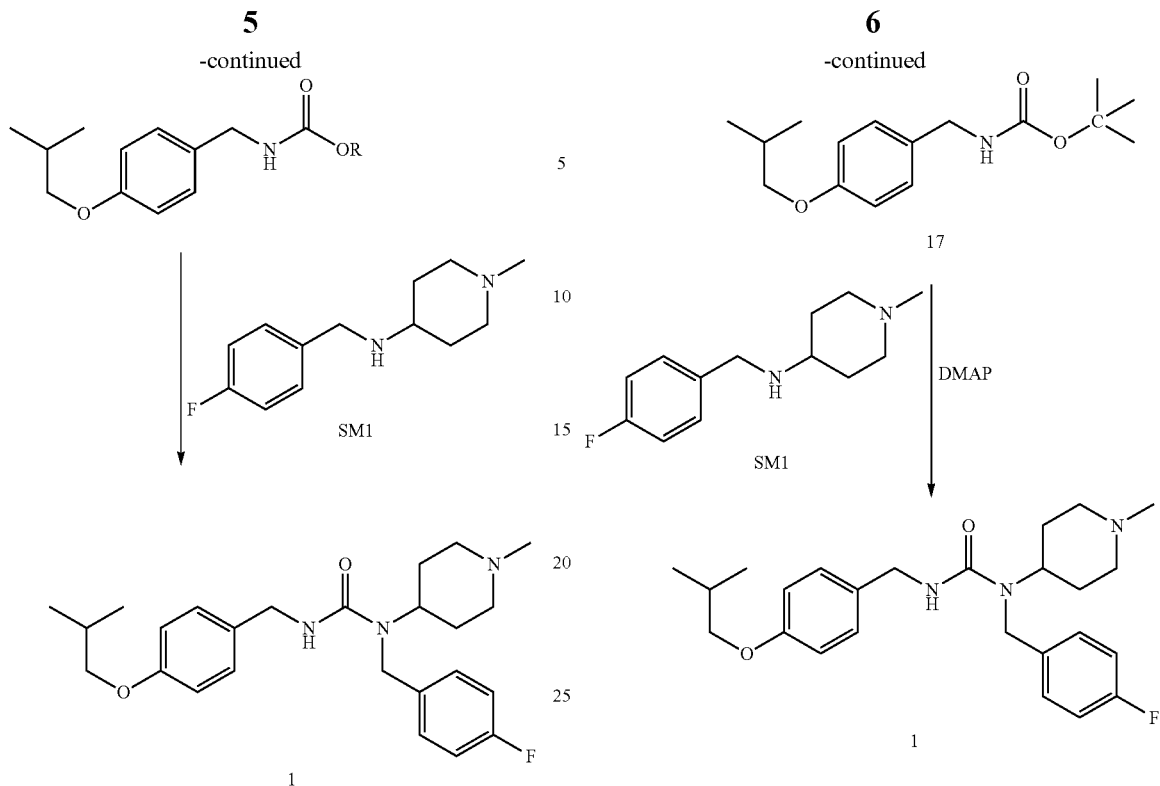

In particular, the carbamates preferably used are methyl carbamate and phenyl carbamate, which are obtained by reacting the amine with the respective carbonates (dimethyl carbonate and diphenyl carbonate) or with chloroformates such as phenyl chloroformate.

It is known from the literature that said reaction takes place with a nucleophilic substitution mechanism, with no need for the formation of stable intermediates (Synthesis, October 1997, p. 1189, Bounkham Thavonekham).

However, example 5d of WO2017015272 describes the preparation of pimavanserin from the intermediate tert-butyl-N-[(4-propan-2-yloxyphenyl)methyl]-carbamate (I) which, apparently because of a breakdown process, generates a mixture in situ, 60-70% of which consists of 1-(isocyanatomethyl)-4-propan-2-yloxybenzene (II), and the remaining 40-30% of the starting product and by-products, before giving rise, with the addition of the final amine, to the desired product. Conversely, in the scheme illustrated in the example and the descriptive part of WO2017015272, no mention is made of the formation of the respective isocyanate, but a synthesis scheme is described which presupposes a substitution mechanism catalysed by DMAP.

Example 5d: Preparation of Pimavanserin Via Using Di-Tert-Butyl Dicarbonate (Boc$_2$O)

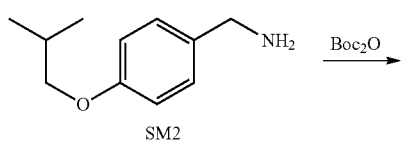

J. Org. Chem. 2014, 79, 4477-4483 describes a synthesis method which gives rise to various ureas other than pimavanserin, starting with tert-butyl-N-carbamates in the presence of triflic anhydride, 2-chloropyridine and triethylamine.

Said reaction leads to the formation of the respective isocyanate which, with the subsequent addition of the amine, gives rise to the desired urea.

The Applicant was unable to isolate the intermediate isocyanate stably, and thus obtain pimavanserin, by replicating the reaction conditions reported in J. Org. Chem. 2014, 79, 4477-4483. The main by-product isolated was the symmetrical urea of formula:

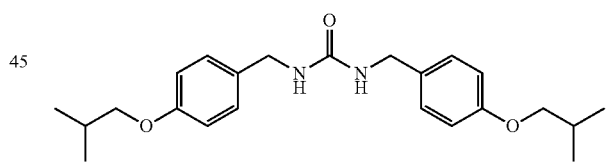

The Applicant's aim was to find a pimavanserin synthesis process, using reagents which are neither toxic nor hazardous, that gives rise to the synthesis of 1-(isocyanatomethyl)-4-propan-2-yloxybenzene of formula II in stable form, with a high degree of purity, in such a way as to obtain the desired pimavanserin with high yields and a high degree of purity, and to optimise the quantities of the reagents used. In particular, the quantity of N-[(4-fluorophenyl)methyl]-1-methylpiperidin-4-amine used in the last reaction step was minimised, leading to a reduction in process costs, because the final pimavanserin can be purified by simple crystallisation, with no need for more expensive purifications, which also involve large losses of yield.

DESCRIPTION OF THE INVENTION

We have surprisingly found that pimavanserin base can be obtained with high purity and high yields by a process that gives rise to the desired product with no need to isolate 1-(isocyanatomethyl)-4-propan-2-yloxybenzene II, an unstable, toxic intermediate, as in the procedure described in U.S. Pat. No. 7,790,899.

Said process also presents numerous advantages, including a single synthesis step, a high overall molar yield, easy purification of the crude end product, and the use of raw materials and reagents which are readily available on the market, inexpensive, and less toxic than those used in the procedures of the prior art cited above.

The process according to the invention (Scheme 3) comprises:

a) converting tert-butyl-N-[(4-propan-2-yloxyphenyl)methyl]carbamate (I)

to 1-(isocyanatomethyl)-4-propan-2-yloxybenzene (II)

in the presence of an organic base and an organic acid or an anhydride of said acid in an organic solvent, to give a solution of (II) in said solvent;

b) adding N-[(4-fluorophenyl)methyl]-1-methylpiperidin-4-amine (IV)

to the solution obtained in a), to give pimavanserin base (V)

c) purifying the pimavanserin base obtained in step b).

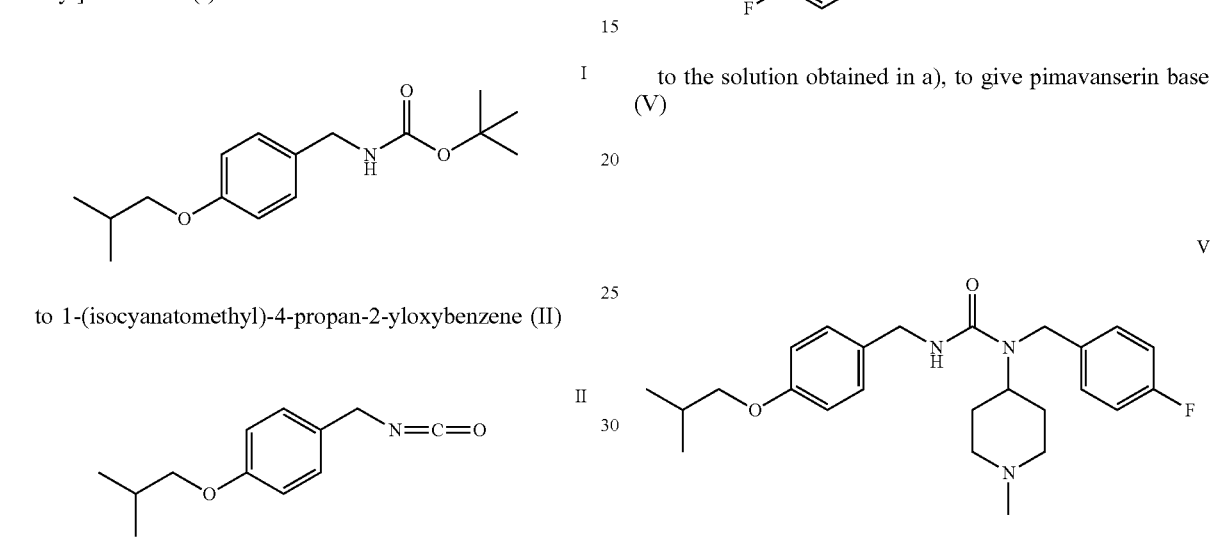

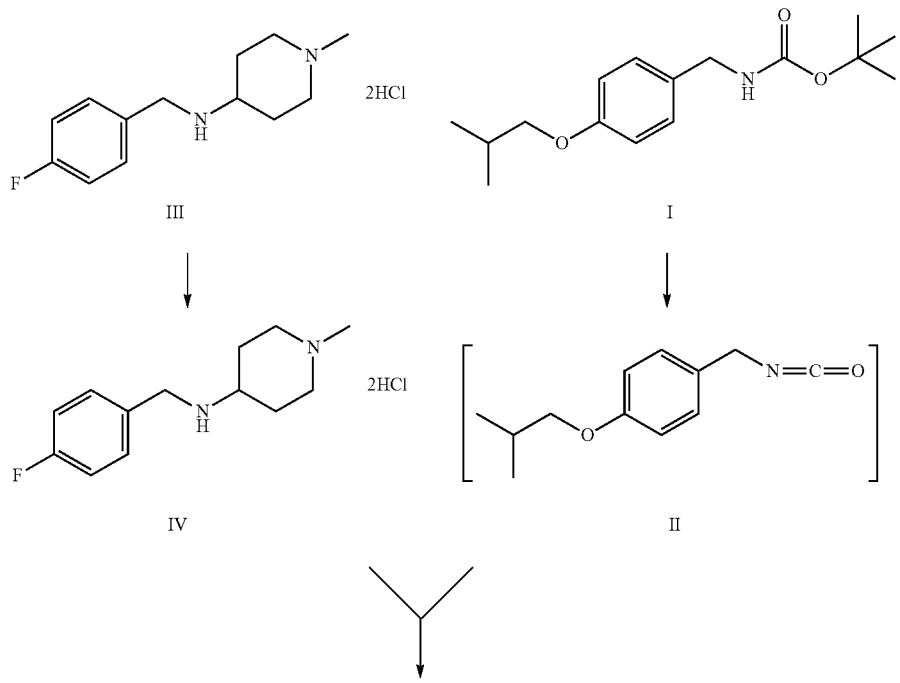

Scheme 3

-continued

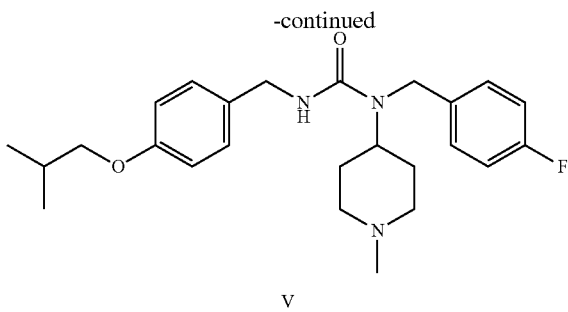

V

Both the starting substrates described in the synthesis process according to the invention are commercially available.

The formation of 1-(isocyanatomethyl)-4-propan-2-yloxybenzene (II) (stage a) is conducted by reacting tert-butyl-N-[(4-propan-2-yloxiphenyl)-methyl]carbamate (I) in a suitable polar aprotic solvent such as tetrahydrofuran, 1,4-dioxane, dichloromethane, tert-butyl methyl ether, diethyl ether, dimethylsulphoxide, dimethylformamide, dimethylacetamide, ethyl acetate, toluene or acetone, more preferably tetrahydrofuran, 1,4-dioxane, dichloromethane, ethyl acetate or toluene, and even more preferably dichloromethane, in the presence of an organic base such as pyridine or 2-chloropyridine, more preferably 2-chloropyridine, with the addition of trifluoroacetic or trifluoromethanesulphonic anhydride, or alternatively trifluoroacetic acid or trifluoromethanesulphonic acid, at a temperature ranging between 0° C. and the boiling point of the solvent, more preferably between 10° C. and 65° C., and even more preferably between 20° C. and 30° C., for a reaction time ranging between 10 min and 3 hours, more preferably between 50 min and 2 hours. The 2-chloropyridine is preferably used in the ratio of 3:1 equivalents relative to tert-butyl-N-[(4-propan-2-yloxiphenyl)methyl]-carbamate (I).

The trifluoromethanesulphonic anhydride is preferably used in the ratio of 1-1.1:1 equivalents relative to tert-butyl-N-[(4-propan-2-yloxiphenyl)methyl]-carbamate (I).

The resulting product (II) is not isolated, and can be used directly in solution for the next step.

The free base of compound (III) is converted by reacting N-[(4-fluorophenyl)methyl]-1-methylpiperidin-4-amine dihydrochloride (III) in a suitable basic aqueous solution, such as aqueous sodium hydroxide or aqueous potassium hydroxide, at a temperature ranging between 0° C. and 100° C., more preferably between 15° C. and 65° C., and even more preferably between 20° C. and 30° C., for a reaction time ranging between 5 min and 1 hour, preferably between 10 min and 30 min. Product (IV) is isolated by extraction from the reaction mixture with a polar aprotic solvent such as tetrahydrofuran, 1,4-dioxane, dichloromethane, tert-butyl methyl ether, diethyl ether, dimethylsulphoxide, dimethylformamide, dimethylacetamide, ethyl acetate, acetone or toluene, more preferably tetrahydrofuran, 1,4-dioxane, dichloromethane, ethyl acetate or toluene, and even more preferably dichloromethane. The solvent is evaporated to obtain the product N-[(4-fluorophenyl)methyl]-1-methylpiperidin-4-amine (IV). Compound (IV) is used in a ratio of 1-1.1:1 equivalents relative to tert-butyl-N-[(4-propan-2-yloxiphenyl)methyl]-carbamate (I).

The formation of (V) is conducted (step b) by reacting the 1-(isocyanatomethyl)-4-propan-2-yloxybenzene (II) with N-[(4-fluorophenyl)methyl]-1-methylpiperidin-4-amine (IV) obtained in step a) in a suitable polar aprotic solvent such as dichloromethane or toluene, at a temperature ranging between 10° C. and 60° C., more preferably between 20° C. and 30° C. The reaction is conducted in the presence of an organic base such as triethylamine, diisopropylethylamine or ethylenediamine, more preferably triethylamine, and reacted for a reaction time ranging between 1 hour and 6 hours, more preferably between 2 hours and 4 hours. The crude product (IV) is isolated by concentrating the solvent at low pressure.

The purification step is preferably performed by crystallisation; the crude reaction product obtained in the preceding step is dissolved in a suitable protic organic solvent such as methanol, and precipitated by adding water. The precipitate is isolated by filtration to obtain pimavanserin base as a white solid with high purity.

The invention will now be further illustrated by the following examples.

Example 1

10.6 ml of 2-chloropyridine and 7.9 ml of methanesulphonic anhydride are added, at 25° C., to a solution of compound I (10.0 g) in dichloromethane (100 ml). The reaction is maintained under stirring at 25° C. for 50 min. The result is complete conversion of compound I to compound II, which is not isolated but used "as is" for the subsequent synthesis step.

Example 2

Compound III (13.35 g) is solubilised in 65 ml of basic aqueous solution (4 g of NaOH) and left under stirring for 10 min at 25° C. During this time, the solution becomes cloudy. 100 ml of dichloromethane is then added at 25° C., and maintained under stirring for 10 min, again at 25° C. The aqueous phase is separated from the organic phase and eliminated, while the organic phase is evaporated to obtain compound IV (10.0 g).

Example 3

15.8 ml of triethylamine is added to the solution of example 1, which is maintained under stirring at 25° C., followed by 10.0 g of compound IV suitably dissolved in 100 ml of dichloromethane. The reaction is maintained under stirring for 3 hours at 25° C. Complete conversion of compound II to compound V is observed, stirring is terminated, and the solvent is evaporated. The resulting crude oil is subsequently purified by crystallisation.

Example 4

The crude compound obtained in the preceding step is solubilised at 25° C. in 100 ml of methanol; the solution is then cooled to between 0° C. and 5° C., and 100 ml of water is dripped into it in about 15 min. A solid forms which is left under stirring at between 0° C. and 5° C. for 1 hour, and then filtered through a Büchner funnel. The solid is washed twice with a 1/1 water/methanol mixture (5 ml). The product is dried under vacuum at 50° C. for 18 h to give a white solid, namely 7.2 g of pimavanserin base.

The invention claimed is:
1. Process for the preparation of pimavanserin base comprising the following steps:
 a) converting tert-butyl-N-[(4-propan-2-yloxyphenyl)methyl]-carbamate (I)

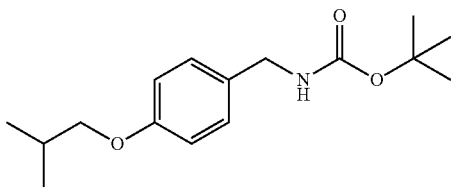

to 1-(isocyanatomethyl)-4-propan-2-yloxybenzene of formula II

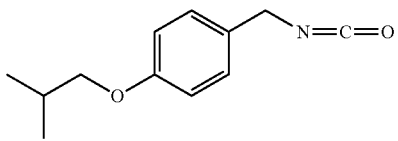

in the presence of an organic base and an organic acid or an anhydride of said acid in an organic solvent, to obtain a solution of (II) in said solvent;
 b) adding N-[4-(fluorophenyl)methyl]-1-methylpiperidin-4-amine (IV)

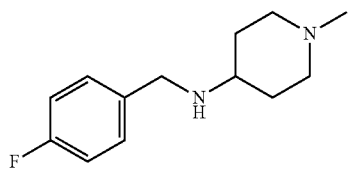

to the solution obtained in a), to obtain pimavanserin base (V)

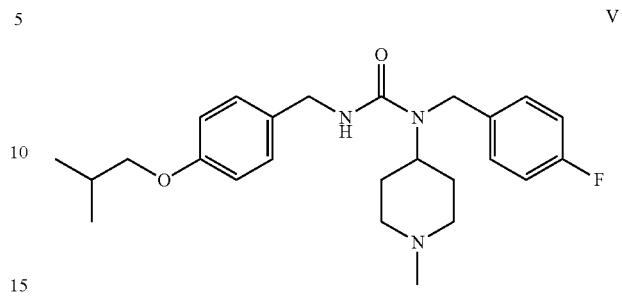

and
 c) purifying the pimavanserin based obtained in step b).
2. The process according to claim 1, wherein the organic base is selected from pyridine and 2-chloropyridine.
3. The process according to claim 1, wherein the organic base is 2-chloropyridine used in a ratio of 3:1 equivalents relative to tert-butyl-N-[(4-propan-2-yloxyphenyl)methyl]-carbamate (I).
4. The process according to claim 1, wherein the organic acid anhydride is selected from trifluoroacetic anhydride and trifluoromethanesulphonic anhydride.
5. The process according to claim 4, wherein the organic acid anhydride is trifluoromethanesulphonic anhydride used in a ratio of 1-1.1:1 equivalents relative to tert-butyl-N-[(4-propan-2-yloxyphenyl)methyl]-carbamate (I).
6. The process according to claim 1, wherein the organic acid is selected from trifluoroacetic acid and trifluoromethanesulphonic acid.
7. The process according to claim 1, wherein compound (IV) is obtained by neutralization of N-[(4-fluorophenyl)methyl]-1-methylpiperidin-4-amine dihydrochloride of formula (III)

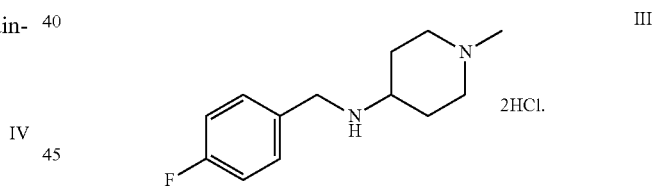

8. The process according to claim 1, wherein compound (IV) is used in a ratio of 1-1.1:1 equivalents relative to tert-butyl-N-[(4-propan-2-yloxyphenyl)methyl]-carbamate (I).

* * * * *